United States Patent [19]

Schachar

[11] 4,452,600

[45] Jun. 5, 1984

[54] CORNEA ENDOTHELIAL PROTECTION METHOD

[76] Inventor: Ronald A. Schachar, 1020 Highway 75 North, Denison, Tex. 75020

[21] Appl. No.: 296,180

[22] Filed: Aug. 25, 1981

Related U.S. Application Data

[63] Continuation-in-part of Ser. No. 34,986, May 1, 1979, abandoned.

[51] Int. Cl.³ .............................................. A61M 5/00
[52] U.S. Cl. ..................... 604/51; 604/173; 604/294
[58] Field of Search ............... 128/303 R, 305, 329 R, 128/329 A; 604/173, 49, 51, 173, 272, 294

[56] References Cited

U.S. PATENT DOCUMENTS

| 2,555,076 | 5/1951 | Crossley | 128/303 R |
| 3,468,602 | 9/1969 | Rosen | 351/160 R |
| 3,595,231 | 7/1971 | Pistor | 604/173 |
| 3,736,938 | 6/1973 | Evvard et al. | 128/305 |
| 3,913,148 | 10/1975 | Potthast | 128/303 R X |
| 3,991,426 | 11/1976 | Flom et al. | 128/303 R X |
| 4,033,349 | 7/1977 | Baehr | 128/303 R |
| 4,053,953 | 8/1977 | Flom et al. | 128/303 R |
| 4,336,805 | 6/1982 | Smirmaul | 128/305 X |

FOREIGN PATENT DOCUMENTS 639548 2/1979 U.S.S.R. ........................... 128/303 R

OTHER PUBLICATIONS

"Four Years' Experience With Binkhorst Lens Implantation", Van Balen, M.D., *American Journal of Ophthalmology*, vol. 75, No. 4, (May 1973), pp. 755-763.

*Primary Examiner*—Michael H. Thaler
*Attorney, Agent, or Firm*—Jerry W. Mills; Gregory M. Howison; Nina Medlock

[57] ABSTRACT

A cornea endotheliam protection device (10) and method for maintaining the curvature of a cornea, for protecting the corneal endothelium and for maintaining anterior chamber pressure is provided. Cornea endothelial protection device (10) includes a plurality of cannulated needles (12) which are fixedly arrayed with respect to one another so that each of cannulated needle members (12) may be inserted through nonoptical portions of the cornea. A manifold (18) is connected to second ends (16) of cannulated needle members (12). A fluid source connected to manifold (18) allows the injection of fluid through cannulated needle members (12) and into the anterior chamber of an eye when cornea endothelial protection device (10) is inserted in position in a human eye.

1 Claim, 6 Drawing Figures

CORNEA ENDOTHELIAL PROTECTION METHOD

CROSS REFERENCE TO OTHER APPLICATIONS

This application is a continuation-in-part of Ser. No. 34,986, filed May 1, 1979 now abandoned and entitled "Cornea Endothelial Protection Device and Method."

TECHNICAL FIELD

This invention relates to intraocular surgery, and more particularly to devices and methods for protection of the corneal endothelium.

BACKGROUND ART

In the past, many techniques have been developed for eye surgery to correct various defects, both traumatic and congenital. For example, several surgical methods and devices for use in cataract surgery are described in U.S. Pat. No. 4,127,903 issued to Schachar and U.S. Pat. No. 4,053,953 issued to Flom, et al.

One type of eye surgery may include, for example, the removal of the natural lens and implantation of an artificial intraocular lens to replace a damaged human lens.

For example, typical surgery for cataracts will generally include forming a standard cataract incision about a portion of the periphery of the cornea. After the incision is made about the periphery of the cornea, the cornea is lifted up to expose the iris and the human lens. In some cases, the human lens is removed and replaced with an artificial intraocular lens.

Part of the surgical implantation procedure may include the injection of fluid into the anterior chamber of the eye so that the iris may be maintained in a flat position while maintaining the curvature of the cornea and maintaining separation between the corneal endothelium and the iris and implanted lens. Similarly, other types of surgical procedures may also require that during or after surgery the corneal endothelium is not allowed to contact the iris or other portion of the human eye or surgical implant. Failure to maintain the corneal endothelium in proper relation can permanently damage the corneal endothelial cells, which can in some cases cause permanent vision defects and in some cases, blindness.

Known methods of injecting air into the anterior chamber of the eye include instilling air through a peripheral corneal incision. Therefore, a need has arisen for a method and apparatus for the injection of a fluid, either liquid or gas, so that the pressure in the anterior chamber of the human eye can be controlled and monitored to facilitate surgical operations and minimize the risk of injury to the eye, particularly to the corneal endothelium, both during and after the surgical procedure.

DISCLOSURE OF THE INVENTION

In accordance with the present invention, a method and apparatus are provided for maintaining corneal curvature during and after intraocular surgery.

In accordance with the present invention, an apparatus and method are provided for introducing a fluid into the anterior chamber of an eye through a plurality of cannulated needle members which extend through the cornea into the anterior chamber of the eye. A fluid source is provided for injecting fluid through the cannulated needle members and into the anterior chamber of the eye. The pressure of the fluid can be regulated so that the desired pressure can be achieved and maintained.

In accordance with another aspect of the present invention, a method and apparatus are provided for irrigation of the anterior chamber during, for example, intraocular surgery.

In accordance with another aspect of the present invention, a method and apparatus are provided for penetrating selected portions of the cornea for injection of a fluid into the anterior chamber of the eye without penetrating the optical zone of the cornea.

In accordance with still another aspect of the present invention a method and apparatus are provided for irrigating and maintaining pressure in the anterior chamber of the eye without the need for suturing the injection sites.

In accordance with still another aspect of the present invention, a method and apparatus are provided for maintaining the iris in a flat position during and after intraocular surgery, and for preventing surgical intraocular implants from unwanted movement.

BRIEF DESCRIPTION OF THE DRAWINGS

A more complete understanding of the invention and its advantages will be apparent from the following detailed description, taken in conjunction with the accompanying drawings, in which.

DETAILED DESCRIPTION

Figure 1:
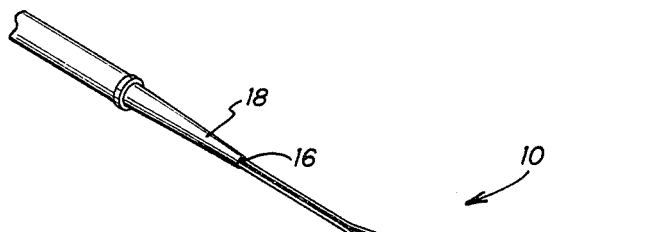
FIG. 1 is a perspective view of one embodiment of the apparatus of the present invention.

FIG. 1 illustrates one embodiment of the cornea endothelial protection apparatus according to the invention and is generally identified by reference numeral 10. Cornea endothelial protection apparatus 10 includes a plurality of cannulated needle members, each identified by reference numeral 12.

Each of cannulated needle members 12 have a first end 14 and a second end 16. First ends 14 are arrayed at spaced apart and predetermined distances so that cornea endothelial protection apparatus 10, when placed in position over a human cornea, can penetrate the cornea at the desired locations. Preferably, first ends 14 are arrayed so that when placed in position in an eye, as will be hereinafter described, first ends 14 penetrate through nonoptical portions of the cornea and preferably approximately normal to the corneal surface at the point of penetration. Although the needle members 12 are shown as being inwardly angled relative to a vertical axis, it is understood that the needle members 12 may be oriented parallel to one another and to the vertical axis. Cannulated needle members 12 are preferably 25 gauge or less in diameter, to avoid the necessity of suturing the perforations caused by piercing the cornea with cornea endothelial protection apparatus 10 after withdrawal from the cornea. Cannulated needle members 12 may be constructed of any material suitable for implantation into the eye, such as stainless steel or polymethylmethacrylate, for example.

Figure 2:
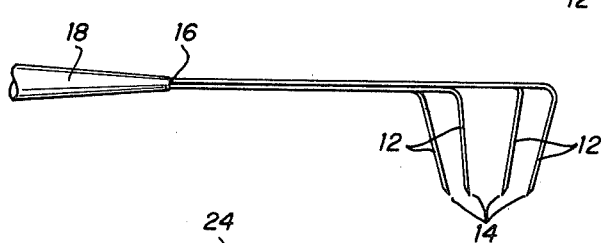
FIG. 2 is a side elevational view of the apparatus shown in FIG. 1.

As shown in FIGS. 1 and 2, cannulated needle members 12 are preferably joined together along a length of cannulated needle members 12 adjacent second ends 16. A manifold 18 is connected to second ends 16 of cannulated needle members 12 as shown in FIGS. 1 and 2. Manifold 18 is supplied fluid from a fluid source (not shown) for injection thereof through cannulated needle members 12 and into the anterior chamber of an eye. Preferably, the fluid source can be regulated so that the desired pressure in the anterior chamber can be maintained both during and after surgery.

Any suitable fluid known to those skilled in the art may be used in accordance with the apparatus and method according to the present invention. For example, gases such as air may be used or liquids may be used such as water, aqueous salt solutions, or other types of irrigating fluids. For most applications, the fluid pressure in the anterior chamber is preferably maintained at from about 15 mm Hg to about 20 mm Hg (gauge). It is anticipated that other applications may require pressures which are either greater or less than the previously mentioned range.

Figure 3:
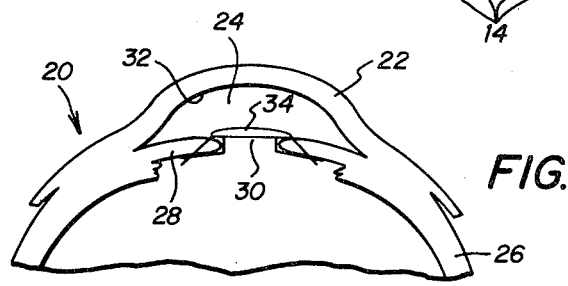
FIG. 3 is a side elevational view of a human eyeball that has had an intraocular lens implanted.

FIG. 3 illustrates a diagrammatic horizontal section through a human eyeball 20 which is partially broken away. As is well known, the eyeball includes a cornea 22 which contains aqueous humor in the anterior chamber 24. A sclera 26 is the tough white supporting tunic of the eyeball and covers the entire eyeball except for cornea 22. The iris 28 is a flimsy tissue which opens and closes to adjust the size of the pupillary aperture 30 in response to the intensity of light striking the eye. The cornea endothelium is indicated by reference numeral 32. Cornea endothelium 32 is the layer of cells on the interior surface of cornea 22. An artificial intraocular lens 34 is also shown implanted on iris 28.

Figure 4:
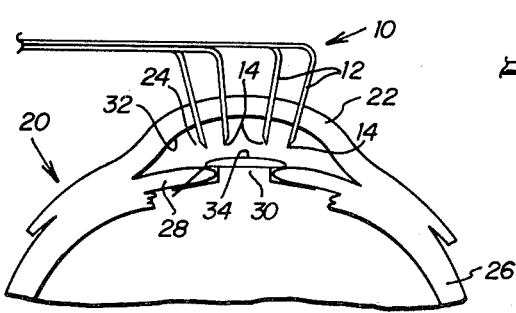
FIG. 4 is a side elevational view of the human eyeball of FIG. 3 showing the apparatus of FIG. 1 penetrating the eye.

FIG. 4 illustrates cornea endothelial protection apparatus 10 inserted through cornea 22 and into anterior chamber 24 where intraocular lens 34 has been affixed. Although FIG. 4 shows the ends of apparatus 10 spaced from lens 34, an important aspect of the invention is that the ends 14 of the apparatus may be placed on lens 34 to prevent unwanted movement or floating of the lens 34 during treatment. Apparatus 10 then serves not only to control the fluid pressure in the eye but to prevent unwanted movement of the lens. Generally, the depth of anterior chamber 24 is approximately 3 millimeters and cannulated needle members 12 of cornea endothelial protection device 10 preferably extend approximately 2 millimeters into the anterior chamber 24. The effective length of cannulated needle members 12 is used herein as the depth into the eye, including the cornea, that the cannulated needle members are able to penetrate. Preferably, the effective length of cannulated needle members 12 is from about 1.0 millimeter to about 3.5 millimeter.

Figure 5:
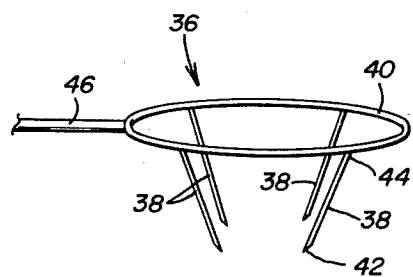
FIG. 5 is a perspective view of an alternate embodiment of the apparatus according to the invention.
Figure 6:
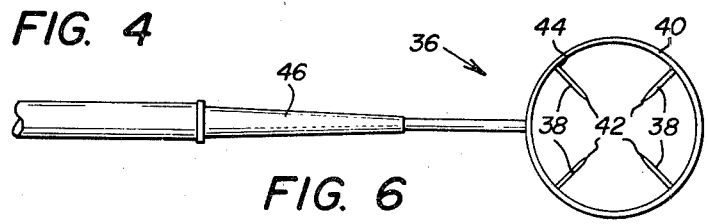
FIG. 6 is a top elevational view of the apparatus of FIG. 5.

FIGS. 5 and 6 illustrate an alternate embodiment of the cornea endothelial protection apparatus according to the invention and is generally referred to by reference numeral 36. As shown in FIG. 5, corneal endothelial protection apparatus 36 includes a plurality of cannulated needle members, each of which needles being referred to by reference numeral 38. Cannulated needle members 38 are of the same dimensions as cannulated needle members 12 of the previously described embodiment. A hollow ring 40 has mounted thereon cannulated needle members 38 which are arrayed to form the desired configuration and separation and are preferably deployed at about 90° intervals. Each of cannulated needle members 38 have a first end 42 and a second end 44. First ends 42 of cannulated needle members 38 penetrate through the cornea when cornea endothelial protection device 36 is inserted into position in an eye. Second ends 44 of cannulated needle members 38 are fixedly attached to hollow ring 40 and the interior of hollow ring 40 communicates with the interior of cannulated needle members 38.

As shown in FIG. 5, a fluid delivery passageway 46 communicates with the interior of hollow ring 40. Fluid delivery passageway 46 is connected to a fluid source so that fluid may be injected through each of cannulated needle members 38 and into the anterior chamber of an eye when cornea endothelial protection apparatus 36 is placed in position through a cornea. The types of fluids and pressures that may be employed with cornea endothelial protection apparatus 36 are identical to those described for cornea endothelial protection apparatus 10.

An alternate embodiment of the invention employs needles which are not cannulated. In this embodiment no fluid is injected into the anterior chamber. A device (not shown) can be constructed similar to cornea endothelial protection apparatus 10 or corneal endothelial protection apparatus 36 but employing noncannulated needles. Such a device can then be placed in position, penetrating the cornea, with the ends of the needles which would be located in the anterior chamber of the eye in contact with a surgical implant such as an intraocular lens for maintaining the intraocular lens in a fixed position and preventing the lens from unwanted movement.

According to the method of the present invention, the anterior pressure of a human eye is controlled during and after eye surgery so that the curvature of the cornea is maintained and the corneal endothelium is protected from contact with the iris or any surgical implant in the anterior chamber. The method according to the present invention also can be used to maintain the iris in a flat position and for irrigation during eye surgery.

A plurality of small apertures are formed in the cornea which extend through the cornea. Preferably, the apertures are located in the nonoptical zone of the cornea. Generally, the optical zone of the cornea is the central circular portion of the cornea which is approximately 4 millimeters in diameter. Cannulated needle members are then inserted through each of the apertures and into the anterior chamber of the eye. The formation of the corneal apertures preferably is accomplished by the insertion of the cannulated needle members through the cornea at the desired locations. Preferably, the cannulated needles are inserted approximately two millimeters into the anterior chamber, the anterior chamber depth normally being from about 2.5 to about 3.0 millimeters.

After insertion of the cannulated needles through the cornea and into the anterior chamber of the eye, a fluid is introduced through the cannulated needles and into the anterior chamber. Preferably, the pressure of fluid in the anterior chamber is monitored by a pressure sensing device which can be located at the fluid source. The pressure can be maintained at the desired level either automatically or manually by any method known to those skilled in the art.

During eye surgery, such as intraocular surgery, the pressure of the anterior chamber may be continuously monitored and maintained at the desired level. During eye surgery this is advantageous since the normal convex corneal curvature can be maintained during intraocular surgery thereby eliminating or greatly reducing the risk of corneal endothelium damage.

After surgery has been completed or when it is no longer necessary to monitor and control the anterior pressure of the eye, the needles which were inserted through the cornea are withdrawn, preferably at the same angle through which they were inserted. Use of needles which are equal to or less than 25 gauge in diameter avoid the need for suturing the corneal perforations upon withdrawal of the cannulated needle members. However, larger diameter cannulated needles may be employed although suturing may be required.

Thus, the method according to the present invention provides a regulated source of irrigation fluid to provide a safe intraocular pressure during and after eye surgery to maintain the curvature of the cornea and protect the corneal endothelium from contacting the iris or any anterior surgical implant.

While the invention has been described with respect to its preferred embodiments, it will be evident that numerous modifications and rearrangements are possible without departing from the scope of the invention.

I claim:

1. A method of protecting the corneal endothelium by maintaining the curvature of the cornea at a spaced apart position from an intraocular lens implant and controlling pressure in the anterior chamber of an eye comprising:

(a) forming a plurality of small apertures which extend through the cornea and into the anterior chamber of the eye by simultaneously inserting a plurality of cannulated needle members into and through the cornea into contact with the lens implant, each of said cannulated needle members having first and second ends, the first ends of said members spaced apart and arrayed for insertion through the cornea and into the anterior chamber of the eye for contact with the lens implant with the second ends of said needle members being arrayed with respect to each other and communicating with a manifold for allowing introduction of a fluid therein from said manifold, said manifold being configured such that frontal access to the central portion of the cornea and the lens implant is unrestricted;

(b) contacting the peripheral regions of the lens implant with said first ends of said needle members in order to prevent movement of the lens implant;

(c) introducing a fluid through said manifold and into said cannulated needle members and into said anterior chamber to increase the pressure in said anterior chamber in order to move the corneal endothelium away from the lens implant while said first ends of said needle members maintain the desired position of the lens implant; and (d) maintaining the pressure of said fluid at a predetermined level.

* * * * *